(12) United States Patent
Kaufhold et al.

(10) Patent No.: US 9,499,474 B2
(45) Date of Patent: Nov. 22, 2016

(54) PROCESS FOR PRODUCING ARYLAMINES

(71) Applicant: Merck Patent GmbH, Darmstadt (DE)

(72) Inventors: Oliver Kaufhold, Darmstadt (DE); Hubert Spreitzer, Viernheim (DE); Stefan Riedmueller, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/357,374

(22) PCT Filed: Oct. 19, 2012

(86) PCT No.: PCT/EP2012/004400
§ 371 (c)(1),
(2) Date: May 9, 2014

(87) PCT Pub. No.: WO2013/068075
PCT Pub. Date: May 16, 2013

(65) Prior Publication Data

US 2014/0309458 A1  Oct. 16, 2014

(30) Foreign Application Priority Data

Nov. 11, 2011 (EP) .................................... 11008986

(51) Int. Cl.
*C07C 209/10* (2006.01)
*C07C 211/61* (2006.01)

(52) U.S. Cl.
CPC .......... *C07C 209/10* (2013.01); *C07C 211/61* (2013.01); *C07C 2103/54* (2013.01)

(58) Field of Classification Search
CPC combination set(s) only.
See application file for complete search history.

(56) References Cited

U.S. PATENT DOCUMENTS

| | | | |
|---|---|---|---|
| 5,576,460 A | 11/1996 | Buchwald et al. | |
| 6,307,087 B1 | 10/2001 | Buchwald et al. | |
| 2009/0261717 A1* | 10/2009 | Buesing .................. | C07C 13/62 257/40 |

FOREIGN PATENT DOCUMENTS

| | | |
|---|---|---|
| CA | 2556850 | 2/2007 |
| WO | WO-2006/074315 A2 | 7/2006 |
| WO | WO-2011/008725 A2 | 1/2011 |

OTHER PUBLICATIONS

Yen et al., Synthesis and Unexpected Electrochemical Behavior of the Triphenylamine-Based Aramids with Ortho- and Para-Trimethyl-Protective Substituents', *Journal of Polymer Science: Part A: Polymer Chemistry*, vol. 48, pp. 5271-5281 (2010).
Rodriguez et al., "Oxaphosphole-Based Monophosphorus Ligands for Palladium-Catalyzed Amination Reactions", *Adv. Synth. Catal.*, vol. 353, pp. 533-537 (2011).
Biscoe, M., et al., "Electronic Effects on the Selectivity of Pd-Catalyzed C—N Bond-Forming Reactions Using Biarylphosphine Ligands: The Competitive Roles of Amine Binding and Acidity", 46 *Angew. Chem., Int. Ed.* 7232-7235 (2007).
Driver, M., et al., "A Second-Generation Catalyst for Aryl Halide Amination: Mixed Secondary Amines from Aryl Halides and Primary Amines Catalyzed by $(DPPF)PdCl_2$", 118 *J. Amer. Chem. Soc.* 7217-7218 (1996).
Guram, A. et al., "A Simple Catalytic Method for the Conversion of Aryl Bromides to Arylamines", 34 *Angew. Chem., Int. Ed.* 1348-1350 (1995).
International Search Report for PCT/EP2012/004400 mailed Feb. 18, 2013.
Kuwano, R., et al., "Palladium-Catalyzed N-Arylation of Bis(ortho-substituted aryl)amines: an Efficient Method for Preparing Sterically Congested Triarylamines", 12 *Synlett*, 1819-1824 (2010).
Louie, J., et al., "Discrete High Molecular Weight Triarylamine Dendrimers Prepared by Palladium-Catalyzed Amination", 119 *J. Amer. Chem. Soc.* 11695-11696 (1997).
Matsuo, K., et al., "N-Alkylation and N-Arylation of Anilines Starting from a Mild N—Mg Reagent: Its Activation Causing the 'N—C' Coupling to Extend the Unified Structure-Reactivity Relationship", 7 *J. Phys. Org. Chem.* 9-17 (1994).
McEwen, W.K., "A Further Study of Extremely WeakAcids", 58 *J. Amer. Chem. Soc.* 1124-1129 (1936).
Paine, A., et al., "Mechanisms and Models for Copper Mediated Nucleophilic Aromatic Substitution. 2. A Single Catalytic Species from Three Different Oxidation States of Copper in an Ullmann Synthesis of Triarylamines", 109 *J. Amer. Chem. Soc.* 1496-1502 (1987).

* cited by examiner

*Primary Examiner* — Clinton Brooks
(74) *Attorney, Agent, or Firm* — Drinker Biddle & Reath LLP

(57) ABSTRACT

The invention relates to a process for producing compounds containing at least one arylamino group by means of a coupling reaction of an amino compound with an aryl compound, using a strong base.

16 Claims, No Drawings

PROCESS FOR PRODUCING ARYLAMINES

CROSS-REFERENCE TO RELATED APPLICATIONS

This application is a national stage application (under 35 U.S.C. §371) of PCT/EP2012/004400, filed Oct. 19, 2012, which claims benefit of European Application No. 11008986.9, filed Nov. 11, 2011, both of which are incorporated herein by reference in their entirely.

The present invention relates to a process for the preparation of compounds containing at least one arylamino group by coupling reaction of an amino compound to an aryl compound using a strong base.

The formation of a bond between a nitrogen atom and an aryl group is a key reaction in organic synthesis. Correspondingly, arylamino compounds are often important intermediates in multistep syntheses. Furthermore, arylamino compounds are used as pharmaceutical active compounds and as functional materials, for example in electronic devices.

In all cases, the achievement of a high yield in the coupling step and the avoidance of by-products is of major importance, since otherwise syntheses on an industrial scale can only be implemented with difficulty. Furthermore, it is vital, in order to achieve high product purity, that side reactions do not occur as far as possible.

The prior art discloses processes for the synthesis of arylamino compounds in which the two starting materials amino compound and aryl compound are brought to reaction with transition-metal catalysis, preferably palladium catalysis, in the presence of a base (Hartwig-Buchwald coupling). Such processes are disclosed, inter alia, in U.S. Pat. No. 5,576,460, in Guram et al., Angew. Chem, Int. Ed. 1995, 43, 1348, in Louie et al., Tet. Lett. 1995, 36, 3609, and in Surry et al., Chem. Sci. 2011, 2, 27.

In spite of the overall good efficiency of these processes and their broad applicability, there is a need for a further development of the method, in particular with respect to slow-reacting and/or bulky starting materials. There is furthermore a need for an improvement in the process with respect to reaction duration, product yield and reduction in the formation of by-products, in particular the formation of defunctionalised aryl compound and/or undesired coupling product with the base employed. The said problems occur, in particular, on use of sterically hindered starting materials, for example ortho-substituted aryl compounds or secondary amino compounds with bulky substituents.

The term "bulky" for the purposes of the present invention is taken to mean that a group or substituent has a large spatial size. The presence of a bulky group typically results in a slowing of reactions in positions which are adjacent to or in the spatial vicinity of the group. In the extreme case, the reaction is slowed so much that it can no longer be utilised preparatively. The term is familiar to the person skilled in the art in the area of organic chemistry. Steric hindrance can be caused by any groups and is greater the larger the spatial size (bulk) of the group. The bulk increases, for example, in the series H, methyl, ethyl, isopropyl, tert-butyl, so that H represents the least bulky group and tert-butyl represents the most bulky group in this series.

Experiments known in the prior art on the further development and optimisation of the method predominantly relate to the use of novel ligand/catalyst systems (cf., inter alia, Surry et al., Chem. Sci. 2011, 2, 27). By contrast, little attention has been paid to a change of the bases typically used. In accordance with the prior art, NaOtBu is typically employed in the Hartwig-Buchwald reaction (in loco citato or Kuwano et al., Synlett 2010, 1819). Furthermore, the use of inorganic bases, such as KOH, NaOH, $Cs_2CO_3$ or $K_3PO_4$, is known in the prior art (see in loco citato).

Surprisingly, it has been found in the course of the present invention that bases having a very high $pK_a$ value are highly suitable for use in transition-metal-catalysed coupling reactions, such as, for example, the Hartwig-Buchwald coupling.

The invention thus relates to a process for the preparation of a compound containing at least one arylamino group, characterised in that the process comprises at least one transition-metal-catalysed coupling reaction between an amino compound and an aryl compound, in which a base having a $pK_a$ value based on dimethyl sulfoxide of at least 33 is employed.

An amino compound in the sense of the present invention is taken to mean an optionally substituted organic compound containing at least one amino group. The amino compound is preferably a diarylamino compound, i.e. a compound in which two aryl groups are bonded to a nitrogen atom which carries a hydrogen atom as third substituent. Particularly preferred embodiments of amino compounds in accordance with the present invention are disclosed in sections below.

An aryl compound in the sense of the present invention is taken to mean an optionally substituted organic compound containing at least one aromatic ring system. Preferred embodiments of aryl compounds in accordance with the present invention are disclosed in sections below.

For the purposes of the present application, the terms "aryl" and "aromatic" in each case also encompass "heteroaryl" and "heteroaromatic", unless a differentiation is made in the explicit case.

An aromatic ring system in the sense of this invention contains 5 to 60 aromatic ring atoms, which may also include heteroatoms. It may be substituted or unsubstituted. The heteroatoms are preferably selected from N, O and/or S. An aromatic ring system in the sense of this invention is intended to be taken to mean a system which does not necessarily contain only aryl groups, but instead in which, in addition, a plurality of aryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triaryl-amine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl groups are linked to one another via single bonds are also taken to be aromatic ring systems in the sense of this invention, such as, for example, systems such as biphenyl, terphenyl or diphenyl-triazine.

An aromatic ring system having 5-60 aromatic ring atoms, which may in each case also be substituted by radicals as defined above and which may be linked to the aromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraaza-perylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

An aryl group in the sense of this invention contains 5 to 60 aromatic ring atoms; it may also contain heteroatoms. The heteroatoms are preferably selected from N, O and S. The aryl group may be substituted or unsubstituted in accordance with the present invention. This represents the basic definition. If other preferences are indicated in the description of the present invention, for example with respect to the number of aromatic ring atoms or the heteroatoms present, these thus apply.

An aryl group here is taken to mean either a simple aromatic ring, i.e. benzene, or a simple heteroaromatic ring, for example pyridine, pyrimidine or thiophene, or a condensed (anellated) aromatic or heteroaromatic polycycle, for example naphthalene, phenanthrene, quinoline or carbazole. A condensed (anellated) aromatic or heteroaromatic polycycle in the sense of the present application consists of two or more simple aromatic or heteroaromatic rings condensed with one another.

An aryl group, which may in each case be substituted by the above-mentioned radicals and which may be linked to the aromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An arylamino group in the sense of the present invention is taken to mean a chemical group in which one or more aromatic ring systems, preferably three aromatic ring systems, are bonded to a nitrogen atom. The arylamino group may be substituted or unsubstituted.

A transition-metal-catalysed coupling reaction in the sense of the present invention is taken to mean a reaction between two organic compounds in which a single bond is formed between the two compounds with transition-metal catalysis. This takes place with formal elimination of a small molecule. Preferably, no further reactions occur on the two compounds. The coupling reaction takes place in accordance with the invention between an amino compound and an aryl compound, where the aryl compound preferably contains a leaving group. The leaving group of the aryl compound is preferably selected from halide, alkylsulfonate, arylsulfonate and diazonlum, particularly preferably from Cl, Br, I, methylsulfonate, trifluoromethylsulfonate, phenylsulfonate and tolylsulfonate. In the coupling reaction, the single bond formed in each case preferably replaces the N—H bond of the amino compound and replaces the bond to the leaving group of the aryl compound. For a more accurate explanation and description of preferred embodiments of the coupling reaction, reference is made to the following sections. Preference is given in accordance with the invention to a transition-metal-catalysed coupling reaction selected from the class of Hartwig-Buchwald reactions, which is known to the person skilled in the art.

For the purposes of the present application, the $pK_a$ value based on dimethyl sulfoxide (DMSO) is taken to mean the $pK_a$ value determined in DMSO or extrapolated in this system.

As is generally known to the person skilled in the art, the $pK_a$ value is the negative decimal logarithm of the value for the equilibrium constant of the deprotonation reaction of an acid. It thus represents a measure of the acid strength. The higher the $pK_a$ value of a compound, the more weakly acidic the compound in question. Conversely, the more basic the conjugated base of the compound, the higher the $pK_a$ value of the compound.

$pK_A$ values can be determined experimentally via the equilibrium constant of the deprotonation reaction. For a detailed description of methods for the experimental determination of $pK_a$ values, reference is made, for example, to McEwen et al., J. Am. Chem. Soc. 1936, 58, 1124.

Furthermore, $pK_A$ values of a multiplicity of compounds are accessible to the person skilled in the art via corresponding reference works and tables. For compounds for which there are no tabulated values, interpolation starting from structurally similar compounds can frequently be carried out, so that $pK_A$ values are also obtainable for such compounds. Alternatively, the person skilled in the art can determine the $pK_a$ value of a non-tabulated compound experimentally by the above-mentioned method.

According to a preferred embodiment of the invention, the base used in the process according to the invention has a $pK_a$ value which is at least a figure of 6 greater than the $pK_a$ value of the amino compound. It particularly preferably has a $pK_a$ value which is at least a figure of 8 greater than the $pK_a$ value of the amino compound. Most preferably, the $pK_a$ value is at least a figure of 10 greater than the $pK_a$ value of the amino compound.

The base used in the process according to the invention preferably has a $pK_a$ value based on dimethyl sulfoxide of at least 34, particularly preferably of at least 36, very particularly preferably of at least 38 and most preferably of at least 40.

Preferred bases for use in the process according to the invention are amides with alkali-metal or alkaline-earth metal counterion, particularly preferably lithium amide, lithium diisopropylamide (LDA), lithium tetramethylpiperidide and lithium pyrrolidide. Preference is furthermore given to organometallic compounds containing a formally negatively charged carbon atom with alkali-metal or alkaline-earth metal counterion, preferably alkali-metal counterion, particularly preferably lithium counterion. Particularly preferred bases are methyllithium, ethyllithium, n-propyllithium, isopropyllithium, n-butyllithium, s-butyllithium, t-butyllithium, n-pentyllithium and isomers thereof, cyclopentyllithium, n-hexyllithium and isomers thereof, phenyllithium and benzyllithium.

The base is preferably employed in an amount of 0.5 to 10 equivalents, based on the molar amount of amino compound employed. Use is particularly preferably made of 0.6 to 5 equivalents, very particularly preferably 0.7 to 2 equivalents and most preferably 0.8 to 1 equivalents of base.

The base is preferably added to the mixture at the beginning of the reaction. This is particularly preferably carried out stepwise, very particularly preferably dropwise, over a period of at least 5 minutes.

A preferred embodiment of the process according to the invention corresponds to the following scheme

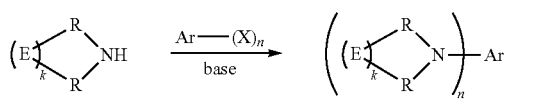

where the following applies to the symbols and indices occurring

Ar is an aromatic ring system having 5 to 60 aromatic ring atoms, which may be substituted by one or more radicals $R^1$;

E is selected on each occurrence, identically or differently, from a single bond, $C(R^1)_2$, C=O, $Si(R^1)_2$, $NR^1$, O and S;

R is selected on each occurrence, identically or differently, from H, a straight-chain alkyl group having 1 to 20 C atoms or a branched or cyclic alkyl group having 3 to 20 C atoms or an alkenyl or alkynyl group having 2 to 20 C atoms, where the above-mentioned groups may each be substituted by one or more radicals $R^1$ and where one or more $CH_2$ groups in the above-mentioned groups may be replaced by —$R^1C$=$CR^1$—, —C≡C—, $Si(R^1)_2$, C=O, C=S, C=$NR^1$, —C(=O)O—, —C(=O)$NR^1$—, $NR^1$, P(=O)($R^1$), —O—, —S—, SO or $SO_2$ and where one or more H atoms in the above-mentioned groups may be replaced by D, F, Cl, Br, I, CN or $NO_2$, or an aromatic ring system having 5 to 60 aromatic ring atoms, which may in each case be substituted by one or more radicals $R^1$, where radicals R may be linked to one another and may form a ring, and where not more than one group R on a nitrogen atom is equal to H;

$R^1$ is selected, identically or differently, on each occurrence from H, D, F, Cl, Br, I, $B(OR^2)_2$, CHO, C(=O) $R^2$, $CR^2$=$C(R^2)_2$, CN, C(=O)$OR^2$, C(=O)$N(R^2)_2$, $Si(R^2)_3$, $N(R^2)_2$, $NO_2$, P(=O)$(R^2)_2$, $OSO_2R^2$, $OR^2$, $S(=O)R^2$, $S(=O)_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups may be replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more H atoms in the above-mentioned groups may be replaced by D, F, Cl, Br, I, CN or $NO_2$, or an aromatic ring system having 5 to 30 aromatic ring atoms, which may in each case be substituted by one or more radicals $R^2$, or an aryloxy group having 5 to 30 aromatic ring atoms, which may be substituted by one or more radicals $R^2$, where two or more radicals $R^1$ may be linked to one another and may form a ring;

$R^2$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^2$ here may be linked to one another and may form a ring;

X is on each occurrence, identically or differently, any desired leaving group;

k is on each occurrence, identically or differently, 0 or 1, where, if k=zero, the group E is not present; and n has a value of 1 to 10; and where the compound of the formula

is the above-mentioned amino compound, the compound of the formula

Ar—(X)$_n$ is the above-mentioned aryl compound, and the compound

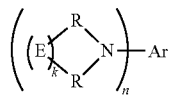

is the above-mentioned compound which contains at least one arylamino group, and the base is generally and preferably as defined above.

It is generally preferred for all groups R to be other than H.

It should furthermore be noted that the process according to the invention is also suitable for the synthesis of oligomeric or polymeric compounds containing at least one arylamino group. The basic reaction scheme shown above including the formation of a bond between a nitrogen atom and an aryl group is furthermore valid for this purpose.

The process according to the invention is preferably used for the preparation of small organic compounds, i.e. compounds having a molecular weight of less than 5000 Da, particularly preferably less than 3000 Da and very particularly preferably less than 2000 Da.

Preferred amino compounds in accordance with the present invention are diarylamino compounds. Preferred amino compounds are furthermore amino compounds in which at least one of the groups R which are bonded to the nitrogen atom is bulky. The term bulky should be understood as defined above. Particularly preferably, both groups R are bulky. Even more preferably, one or both groups R represent an aryl group which carries a substituent in the ortho-position to the bond to the nitrogen atom, or an aryl group which carries a condensed-on ring in the ortho-position to the bond to the nitrogen atom.

The radical R is preferably selected, identically or differently, on each occurrence from a straight-chain alkyl group having 1 to 10 C atoms or a branched or cyclic alkyl group having 3 to 10 C atoms or an alkenyl or alkynyl group having 2 to 10 C atoms, where the above-mentioned groups may each be substituted by one or more radicals $R^1$ and where one or more $CH_2$ groups in the above-mentioned groups may be replaced by $-R^1C=CR^1-$, $-C\equiv C-$, $Si(R^1)_2$, $C=O$, $NR^1$, $P(=O)(R^1)$, $-O-$, $-S-$, SO or $SO_2$ and where one or more H atoms in the above-mentioned groups may be replaced by D, F, Cl or CN, or an aromatic ring system having 5 to 30 aromatic ring atoms, which may in each case be substituted by one or more radicals $R^1$, where radicals R may be linked to one another and may form a ring.

R particularly preferably represents an aromatic ring system having 5 to 18 aromatic ring atoms, which may be substituted by one or more radicals $R^1$. R is very particularly preferably equal to phenyl or naphthyl, which may be substituted by one or more radicals $R^1$.

R furthermore preferably represents an aromatic ring system having 5 to 18 aromatic ring atoms which contains at least one radical $R^1$ which is other than H and D in the ortho-position to the bond to the nitrogen atom.

R furthermore preferably represents an aryl group having 10 to 18 aromatic ring atoms which contains at least two aromatic rings condensed with one another, where the one aromatic ring is condensed onto the other aromatic ring in an ortho-position to the bond to the nitrogen atom.

$R^1$ is preferably selected on each occurrence, identically or differently, from H, D, F, CN, $Si(R^2)_3$, $N(R^2)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^2$ and where one or more $CH_2$ groups in the above-mentioned groups may be replaced by $-C\equiv C-$, $-R^2C=CR^2-$, $Si(R^2)_2$, $C=O$, $C=NR^2$, $-NR^2-$, $-O-$, $-S-$, $-C(=O)O-$ or $-C(=O)NR^2-$, or an aromatic ring system having 5 to 20 aromatic ring atoms, which may in each case be substituted by one or more radicals $R^2$, where two or more radicals $R^1$ may be linked to one another and may form a ring.

The radical $R^1$ which is bonded in the ortho-position to the bond to the nitrogen atom is particularly preferably selected from alkyl groups having 1 to 10 C atoms, which may be substituted by one or more radicals $R^2$, and aryl groups having 5 to 18 aromatic ring atoms, which may be substituted by one or more radicals $R^2$.

E is preferably a single bond.

X is selected on each occurrence, identically or differently, from Cl, Br, I, methylsulfonate, trifluoromethylsulfonate, phenylsulfonate, tolylsulfonate and diazonium.

The index n is preferably equal to 1, 2, 3, 4 or 5, particularly preferably equal to 1 or 2 and very particularly preferably equal to 1.

A preferred embodiment for the amino compound conforms to the following formula (N)

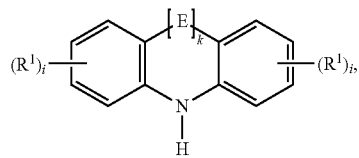

where $R^1$ is as defined above, E represents a single bond, k is equal to 0 or 1, and i has on each occurrence, identically or differently, a value of 0 to 5 and denotes the number of groups $R^1$ bonded to the phenyl ring. Preferably, at least one index i per formula (N) has a value of 1 to 5. The amino compound of the formula (N) preferably contains at least one group $R^1$ bonded in the ortho-position to the amino group. If k is equal to zero, the group E is not present.

Particularly preferred embodiments of amino compounds are the compounds of the formulae (N-1) to (N-26) shown below

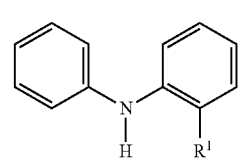

formula (N-1)

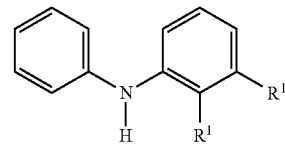

formula (N-2)

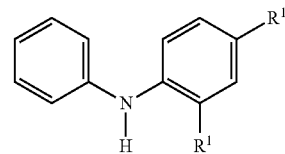

formula (N-3)

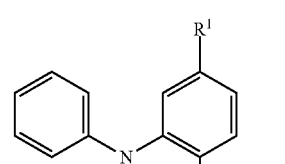

formula (N-4)

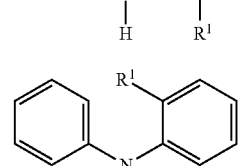

formula (N-5)

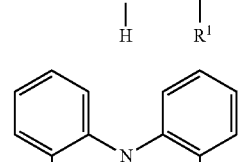

formula (N-6)

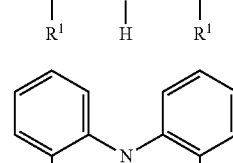

formula (N-7)

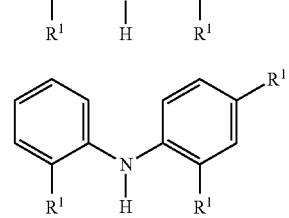

formula (N-8)

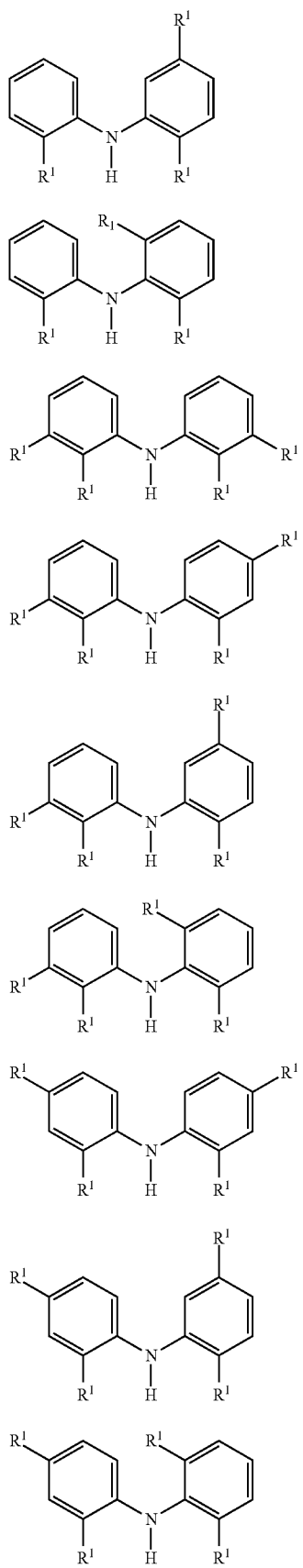
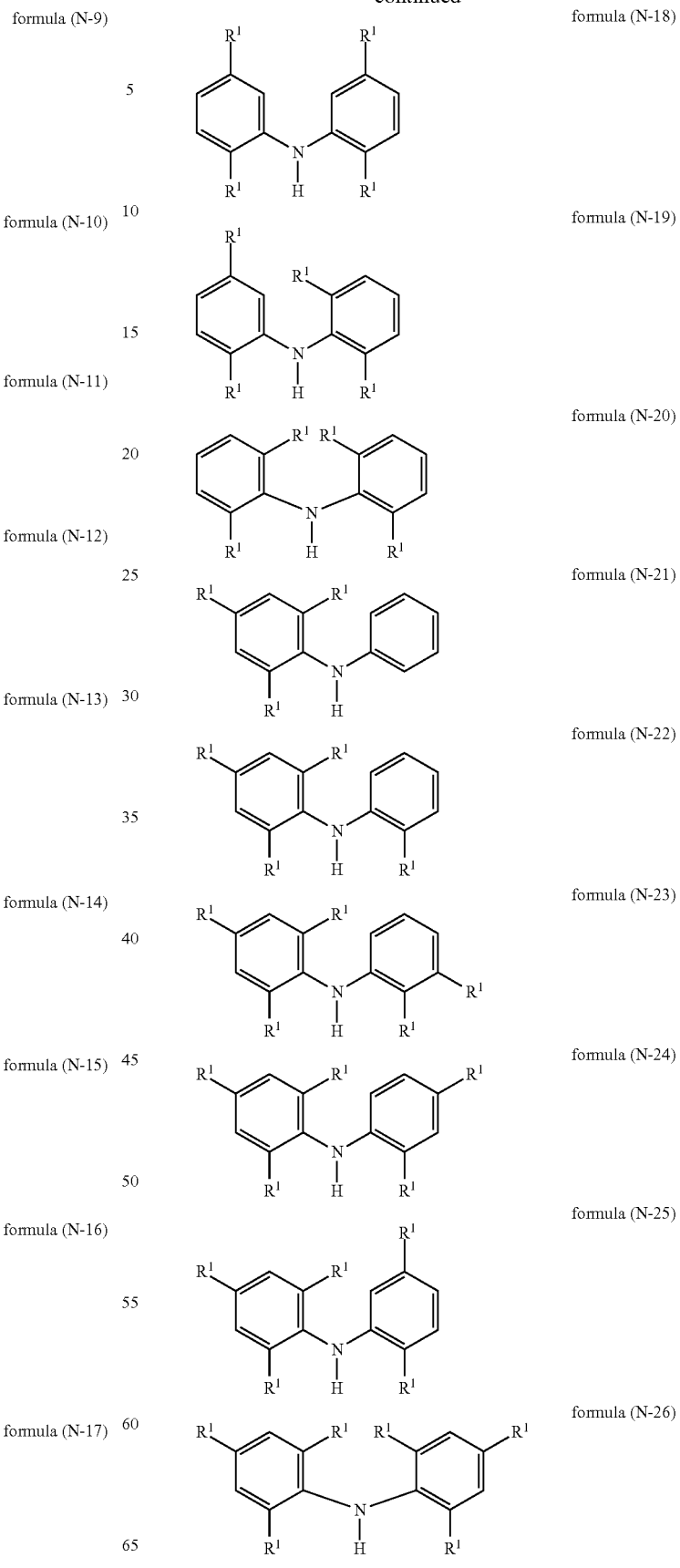

where R¹ is as defined above and is other than H and D.

Preferred embodiments of amino compounds are furthermore the compounds of the formulae (N-27) to (N-38) shown below formula (N-27)
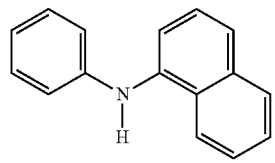

formula (N-28)
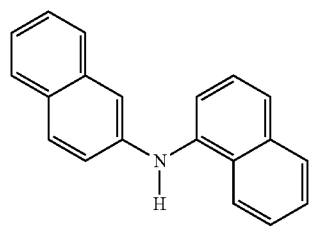

formula (N-29)
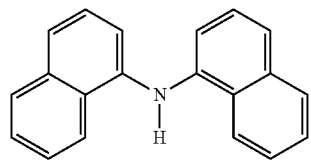

formula (N-30)
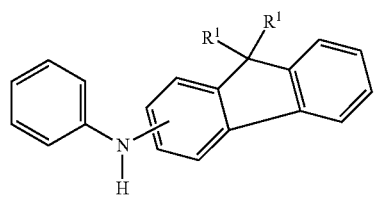

formula (N-31)
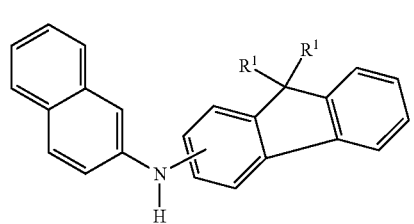

formula (N-32)
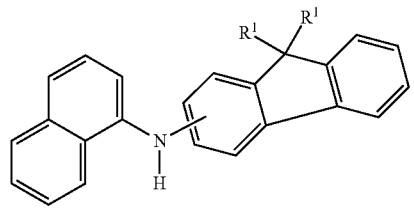

formula (N-33)
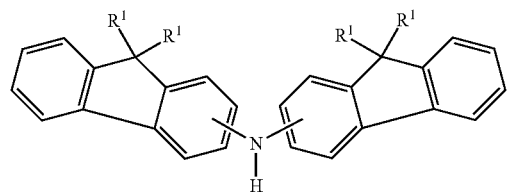

formula (N-34)
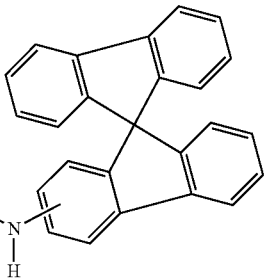

formula (N-35)
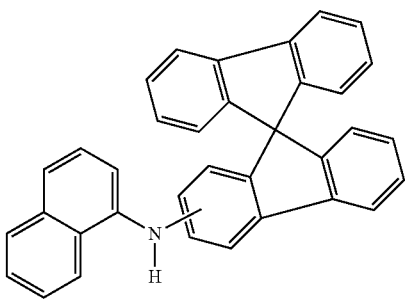

formula (N-36)
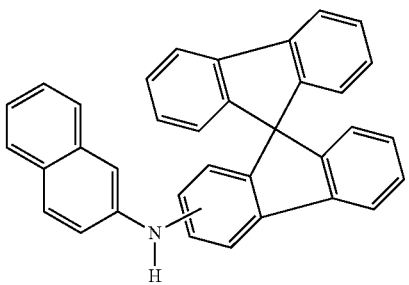

formula (N-37)
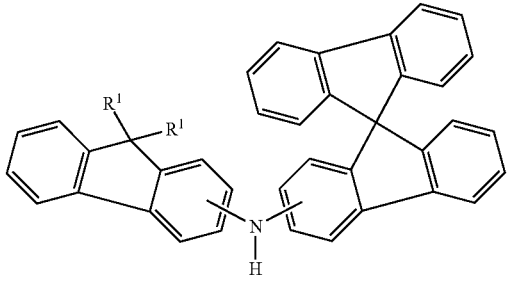

formula (N-38)
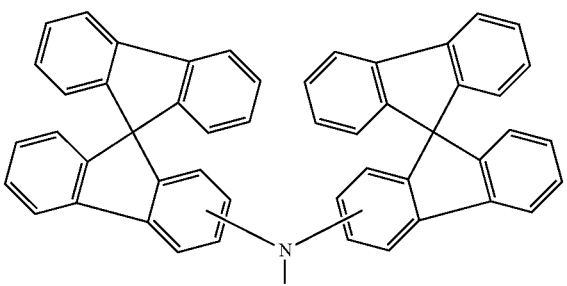

where the compounds may be substituted at all positions depicted as unsubstituted by a radical R¹ which is selected from the embodiments shown above, and where the fluorenyl and spirobifluorenyl groups may be bonded in any desired position on their aromatic six-membered ring.

The group Ar preferably represents an aromatic ring system having 5 to 30 aromatic ring atoms, which may be substituted by one or more radicals $R^1$.

In general, bulky groups Ar are preferred in accordance with the invention in the aryl compounds Ar—$(X)_n$, as are groups Ar which are substituted by bulky groups $R^1$, preferably in the ortho-position to the bond to the leaving group X.

The group Ar preferably contains at least one radical $R^1$ which is other than H and D and is selected from the embodiments of $R^1$ shown above in the ortho-position to the bond to the leaving group X.

The radical $R^1$ which is bonded to the group Ar in the ortho-position to the bond to the nitrogen atom is particularly preferably selected from alkyl groups having 1 to 10 C atoms, which may be substituted by one or more radicals $R^2$, and aryl groups having 5 to 18 aromatic ring atoms, which may be substituted by one or more radicals $R^2$.

Ar furthermore preferably represents an aromatic ring system having 10 to 30 aromatic ring atoms which contains at least two aromatic rings condensed with one another, where the one aromatic ring is condensed onto the other aromatic ring in an ortho-position to the bond to the nitrogen atom.

Ar as constituent of the aryl compound Ar—$(X)_n$ preferably includes a condensed aryl group selected from naphthalene, anthracene, phenanthrene, pyrene, chrysene, perylene, fluoranthene, benzanthracene, benzophenanthrene, tetracene, pentacene, benzopyrene, acridine and phenanthridine. Ar as constituent of the aryl compound Ar—$(X)_n$ likewise preferably includes an aromatic ring system selected from fluorene, spirobifluorene, cis- or trans-indenofluorene, cis- or trans-indolocarbazole, cis- or trans-indenocarbazole, cis- or trans-monobenzindenofluorene and cis- or trans-dibenzindenofluorene.

Particularly preferred groups Ar as constituent of the aryl compound Ar—$(X)_n$ conform to the following formulae (A-1) to (A-23)

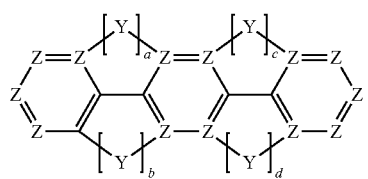

formula (A-1)

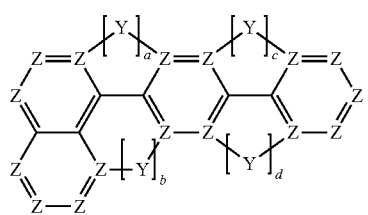

formula (A-2)

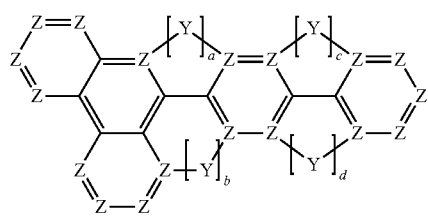

formula (A-3)

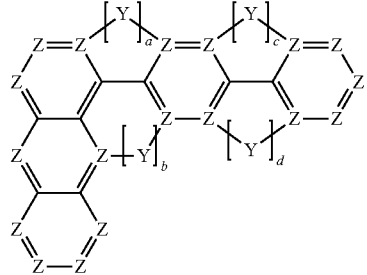

formula (A-4)

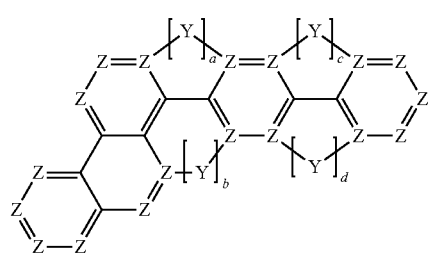

formula (A-5)

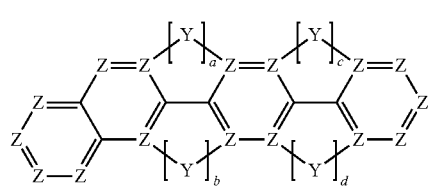

formula (A-6)

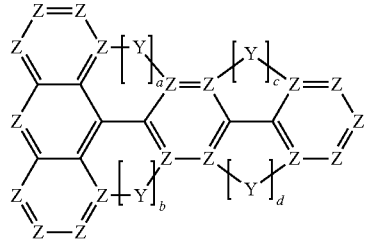

formula (A-7)

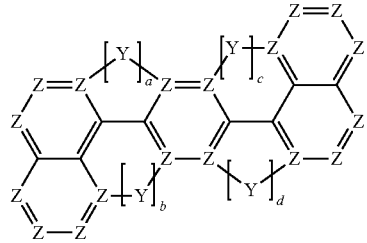

formula (A-8)

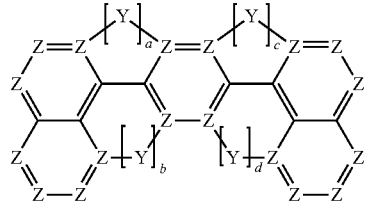

formula (A-9)

formula (A-10)
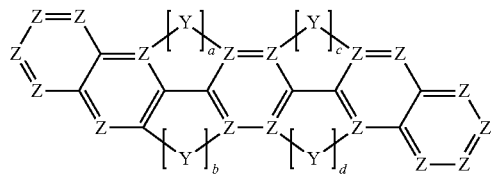
formula (A-11)
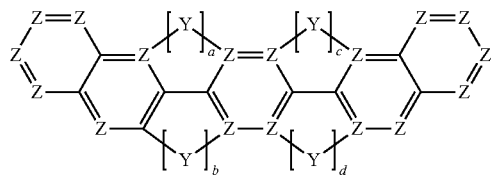
formula (A-12)
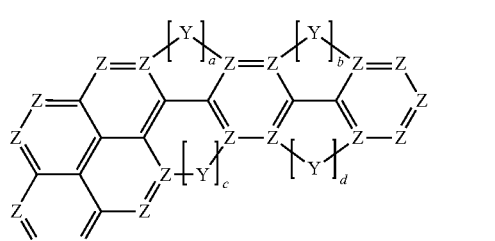
formula (A-13)
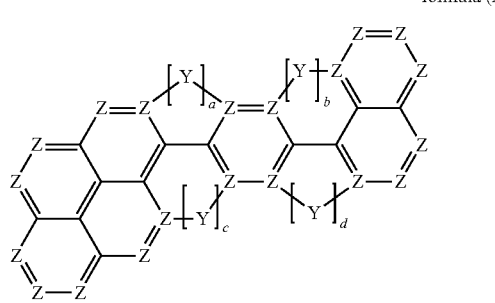
formula (A-14)
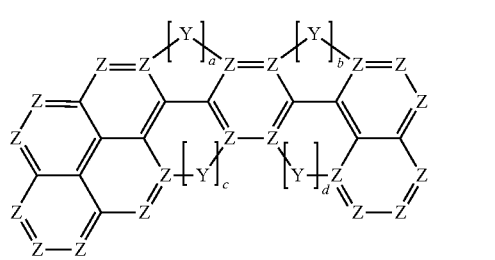
formula (A-15)
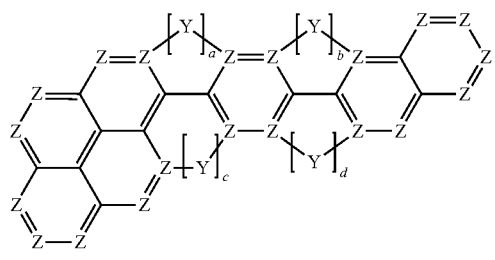
formula (A-16)
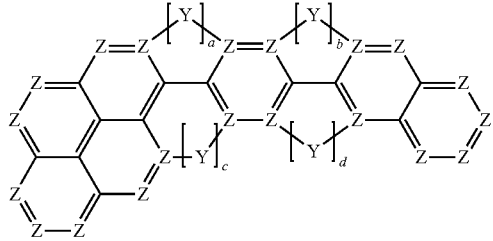
formula (A-17)
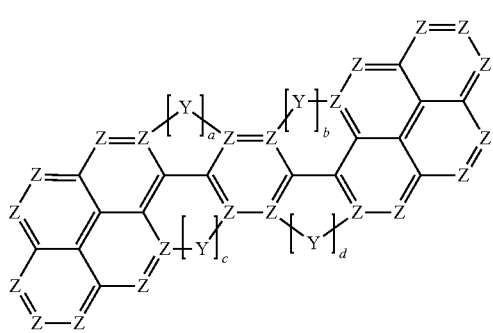
formula (A-18)
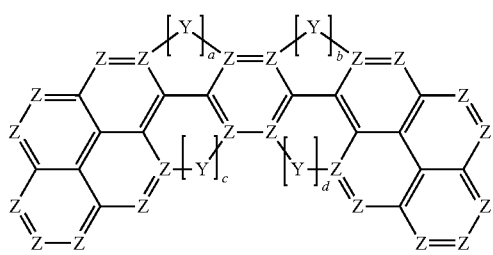
formula (A-19)
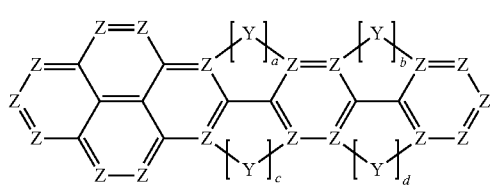
formula (A-20)
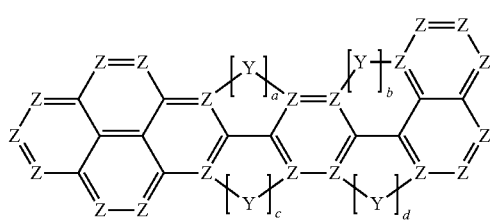
formula (A-21)
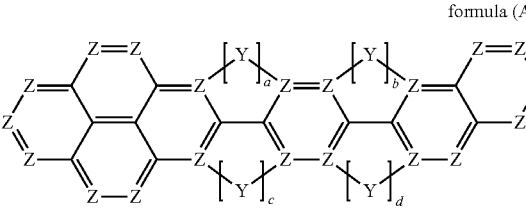

-continued

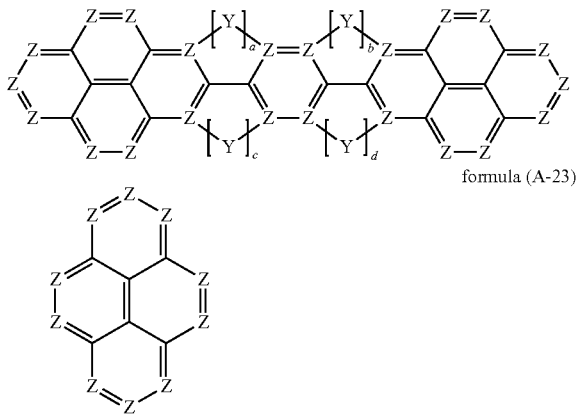

formula (A-22)

formula (A-23)

where the following applies to the symbols and indices occurring:

Z is on each occurrence, identically or differently, $CR^1$ or N if no group X or Y is bonded, and is equal to C if a group X or Y is bonded;

Y is selected on each occurrence, identically or differently, from $B(R^1)$, $C(R^1)_2$, $Si(R^1)_2$, C=O, C=NR$^1$, C=C(R$^1$)$_2$, O, S, S=O, SO$_2$, N(R$^1$), P(R$^1$) and P(=O)R$^1$;

$R^1$ is defined as indicated above; and a, b, c and d are on each occurrence, identically or differently, 0 or 1, where the sum of a and b is greater than zero and the sum of c and d is greater than zero.

The group X in the aryl compounds Ar—(X)$_n$ can be bonded at any desired position on the group Ar. In the groups Ar of the formulae (A-1) to (A-22), it is preferably bonded to a group Z.

The compounds containing at least one arylamino group obtained in the reaction (products) are characterised in that a bond Ar—N occurs instead of the bond Ar—(X)$_n$ of the aryl compound, where N denotes the nitrogen atom of the amino compound. Preferred process products of the process according to the invention are thus combinations of the above-mentioned preferred starting materials aryl compound and amino compound. Particular preference is given to coupling products resulting from combinations of the compounds of the preferred formulae (A-1) to (A-23) and (N-1) to (N-38).

In the process according to the invention, a transition-metal catalyst is employed. This can be added either at the beginning of the reaction or at any desired later point in time. The catalyst is preferably already present in the mixture when the base is added. However, it may also be preferred for the catalyst not to be added to the mixture until a later point in time, for example after completed addition of the base.

For clarity, it should be noted that the term "catalyst" in the sense of the present application is taken to mean both an actually catalytically active species and also a catalyst precursor which forms the catalytically active species in the reaction mixture.

Preferred catalysts for the purposes of the present application are homogeneous catalysts. Homogeneous catalysts are taken to mean catalysts which are present in dissolved form in the reaction medium.

It is furthermore preferred for the catalyst to be a compound which contains at least one transition metal selected from groups 7, 8, 9, 10 and 11 of the Periodic Table. The catalyst is particularly preferably a compound which contains at least one metal selected from iron, nickel, copper, palladium and platinum, where palladium is preferred.

The catalyst is preferably employed in an amount of 0.001 to 10.0 mol-%, particularly preferably 0.01 to 5.0 mol-%, very particularly preferably 0.1 to 2.0 mol-%.

The catalyst preferably comprises one or more metals and one or more ligands. The catalyst may be added as a single compound comprising both the metal and also one or more ligands. Alternatively, the catalyst may be formed in situ in the reaction mixture from separately added metal compound and ligand compound.

In an alternative embodiment, exclusively a metal compound or elemental metal is used as catalyst without the use of ligands.

Preferred compounds as catalyst constituents or as independent catalysts without additional ligands are selected from PdCl$_2$, Pd(OAc)$_2$, (CH$_3$CN)$_2$—PdCl$_2$, Pd(PPh$_3$)$_4$, bis(dibenzylideneacetone)dipalladium (Pd$_2$(dba)$_2$), tris(dibenzylideneacetone)dipalladium (Pd$_2$(dba)$_3$), Ni(acac)$_2$, NiCl$_2$[P(C$_5$H$_5$)$_3$]$_2$, Ni(1,5-cyclooctadiene)$_2$, Ni(1,10-phenanthroline)$_2$, Ni(dppf)$_2$, NiCl$_2$(dppf) and NiCl$_2$(1,10-phenanthroline). Furthermore, Pd/C, polymer-stabilised Pd and Raney nickel can be used.

Preferred ligands are selected from monodentate and oligodentate ligands. According to a preferred embodiment, chelating ligands are used. Preferred ligands are selected from phosphines, amines, aminophosphines and N-heterocyclic carbenes. Preferred phosphines and amines for use as ligands are disclosed in WO 2011/008725, WO 2006/074315 and U.S. Pat. No. 6,307,087. Preferred N-heterocyclic carbenes for use as ligands are disclosed in CA 2556850. Particularly preferred N-heterocyclic carbenes are the carbenes disclosed in the said application as ligands of structures 1a to 1n, as defined therein.

Particularly preferred phosphines as ligands are selected from dicyclohexylphosphino-2',6'-dimethoxybiphenyl, dicyclohexylphosphino-2',6'-diisopropoxybiphenyl, di-tert-butyl(2',4',6'-triisopropyl-3,6-dimethoxybiphenyl-2-yl)phosphine, dicyclohexyl(2',4',6'-triisopropyl-3,6-dimethoxybiphenyl-2-yl)phosphine, trimethylphosphine, triethylphosphine, tripropylphosphine, triisopropylphosphine, tributylphosphine, tri-tert-butyl-phosphine, tricyclohexylphosphine, triphenylphosphine, di-tert-butylchlorophosphine, trimethyl phosphite, triethyl phosphite, tripropyl phosphite, triisopropyl phosphite, tributyl phosphite, tricyclohexyl phosphite, triphenylphosphine, tri(o-tolyl)phosphine, triisopropylphosphine, tricyclohexylphosphine, 2,2'-bis-(diphenylphosphino)-1,1'-binaphthyl (BINAP), 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)butane, 2,4-bis(dicyclohexylphosphino)pentane and 1,1'-bis(diphenylphosphino)ferrocene.

Particularly preferred amines as ligands are 2,2'-bipyridine (bipy), 1,10-phenanthroline and tetramethylethylenediamine.

The process according to the invention is preferably carried out in liquid phase. Any desired organic solvent can be employed here, in particular those which are not deprotonated or only deprotonated to a slight extent by the base used. Preference is given to the solvents known to the person skilled in the art in the area of organic synthesis with suitability for use in transition-metal-catalysed coupling reactions. Suitability for use in the reactions according to the invention is taken to mean, in particular, inertness to the reaction conditions.

Particularly preferred solvents are selected from benzene, toluene, 1,2-xylene, 1,3-xylene, 1,4-xylene, mesitylene, tetrahydrofuran (THF), 1,4-dioxane, dimethoxyethane (dme) and bis(2-methoxyethyl)ether (diglyme). Anhydrous solvents are preferably employed.

The reaction can be carried out under atmospheric pressure or under superatmospheric pressure.

According to a preferred embodiment, the reaction is carried out under inert-gas atmosphere, for example under nitrogen or argon atmosphere.

The reaction duration is typically between a few minutes and a few days, preferably between a few minutes and 100 hours, very particularly preferably between 15 minutes and 80 hours. The times indicated relate to the total duration of the reaction.

The reaction temperature is preferably between 0 and 300° C., particularly preferably between 20 and 200° C., very particularly preferably between 60 and 150° C. and even more preferably between 100 and 130° C. The reaction temperatures indicated relate to the main phase of the reaction, during which all components are present in the mixture and the bond formation takes place with catalysis.

Typically, the base dissolved in a solvent is added to the mixture at the beginning of the reaction. The solvent used here is preferably one of the solvents indicated as preferred for the reaction. The addition is preferably carried out stepwise, particularly preferably dropwise over a period of at least 5 minutes. During this phase of the reaction, the reaction temperature is preferably significantly lower than during the main phase of the reaction. During this phase of the reaction, it is particularly preferably between −70° C. and 40° C., very particularly preferably between −20° C. and 30° C., most preferably between 0° C. and 25° C.

The general reaction procedure and work-up and the equipment and reaction vessels used are not specified in greater detail. The person skilled in the art will be able to select suitable embodiments taking into account the working examples and drawing on his general expert knowledge. Particularly suitable methods are those as are generally known to the person skilled in the art for Hartwig-Buchwald couplings and similar reactions.

According to a preferred variant of the reaction procedure, firstly the amino compound, the aryl compound and the catalyst are dissolved or suspended in the solvent. The base is subsequently added to the mixture, preferably stepwise, as indicated above.

According to a further variant of the reaction procedure, a base is added to the amino compound before the aryl compound is present in the reaction mixture. The aryl compound is added in a later step.

This variant of the process according to the invention can be depicted diagrammatically as follows:

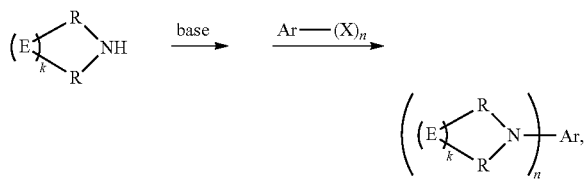

where the groups occurring are as defined above. In this variant, the same preferences as indicated above apply in relation to the starting materials, the base and the catalyst compound.

According to this variant of the process according to the invention, firstly the amino compound and the base are brought to reaction with one another. The aryl compound here is still not present in the mixture. This phase is called the first phase of the reaction. During this phase, the catalyst may already be present in the mixture.

In a second phase of the reaction, the aryl compound is added. The catalyst is preferably also not added until this phase of the reaction, but it may also have already been added to the mixture beforehand.

The products obtained in the process according to the invention are preferably employed as functional materials in electronic devices. The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The process products obtained are preferably used as hole-transport materials and/or as singlet emitter materials and/or as electron-blocking materials and/or as matrix materials in electronic devices. However, other uses are also possible, depending on the basic structure of the products and the substituents present in addition to the amino group.

The present invention furthermore relates to the use of a base having a pKa value of at least 33 based on dimethyl sulfoxide in a transition-metal-catalysed coupling reaction between an amino compound and an aryl compound.

The amino compound and the aryl compound are defined here as indicated above.

The base here preferably has a $pK_a$ value based on dimethyl sulfoxide of at least 34, particularly preferably of at least 36, very particularly preferably of at least 38 and most preferably of at least 40.

It is furthermore preferred for the compounds obtained in the coupling reaction to be functional materials for electronic devices, particularly preferably functional materials for organic electroluminescent devices (OLEDs).

The use according to the invention of a base having a pKa value based on dimethyl sulfoxide of at least 33 results in excellent purity of the compounds obtained. This is of high importance for the use of the compounds as functional materials in electronic devices. Furthermore, the formation of by-products, which, even in small amount, have an adverse effect on the performance data of the electronic device, is suppressed by the use of a base of this type.

In general, it is of major importance for the use of organic compounds in electronic devices that the compounds can be prepared in high purity. It is furthermore necessary for industrial use that the compounds can be prepared on a large scale, preferably of greater than 100 g, particularly preferably of greater than one kilogram.

In order to achieve these aims, high robustness and efficiency of the synthesis process is vital. In particular, a high yield of product and the lowest possible formation of by-products are desirable.

The process according to the invention is distinguished, inter alia, by the fact that a high yield of product and low formation of by-products occurs. In particular, only little by-product in the form of a defunctionalisation or coupling of the base used is observed on use of bulky amino compounds and aryl compounds as starting materials in the process according to the invention. A yield of product of greater than 80% is particularly preferably achieved, and less than 20% of by-products, based on the amount of starting materials employed, occur. The yield of product obtained is very particularly preferably greater than 90%, and less than 10% of by-products, based on the amount of starting materials employed, occur.

Furthermore, the process can be carried out with a small amount of catalyst employed and under mild reaction conditions.

The following working examples serve for illustration and detailed description of the invention.

WORKING EXAMPLES

A) Comparative Example 1

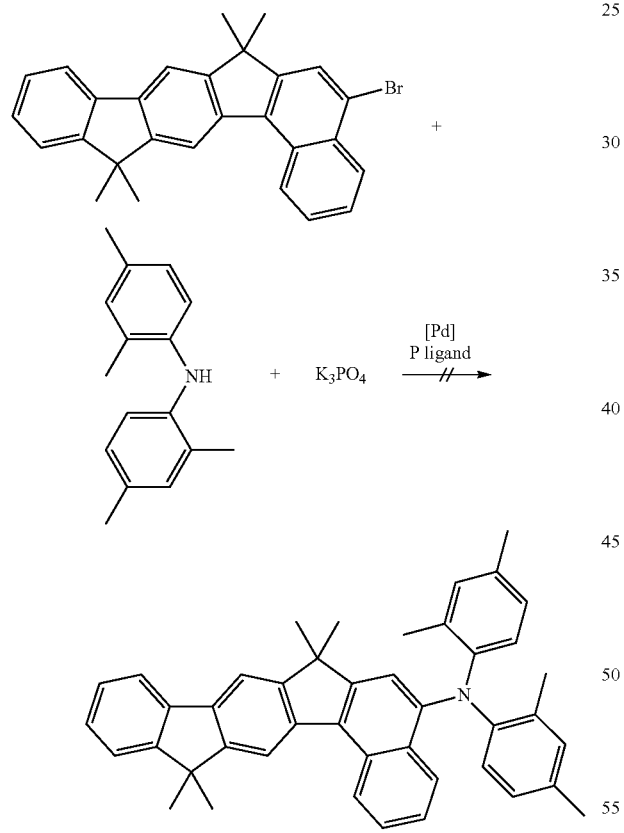

A mixture of powdered tripotassium phosphate (12 eq.), bis(2,4-dimethylphenyl)amine (1.25 eq), 1,2-benzo-3-bromo-6,6,12,12-tetramethyl-6,12-dihydroindeno[1,2-b]fluorene (1 eq), Pd(OAc)$_2$ (0.02 eq) and 2-(dicyclohexylphosphino)-2',6'-dimethoxy)biphenyl (S-Phos, 0.04 eq) in toluene is heated under reflux for 60 h. TLC monitoring of the reaction mixture shows no reaction.

Further examples with variation of ligand and base within the class of carbonate and phosphate salts:

| Pd source | [P] ligand | Base | Ar | Yield [%] |
|---|---|---|---|---|
| Pd(OAc)$_2$ | S-Phos | K$_3$PO$_4$ | 2,4-dimethylphenyl | 0 |
| Pd(OAc)$_2$ | S-Phos | K$_2$CO$_3$ | 2,4-dimethylphenyl | 0 |
| Pd(OAc)$_2$ | S-Phos | Cs$_2$CO$_3$ | 2,4-dimethylphenyl | 0 |
| Pd(OAc)$_2$ | Ru-Phos | K$_3$PO$_4$ | 2,4-dimethylphenyl | 0 |
| Pd(OAc)$_2$ | Ru-Phos | K$_2$CO$_3$ | 2,4-dimethylphenyl | 0 |
| Pd(OAc)$_2$ | Ru-Phos | Cs$_2$CO$_3$ | 2,4-dimethylphenyl | 0 |

B) Comparative Example 2

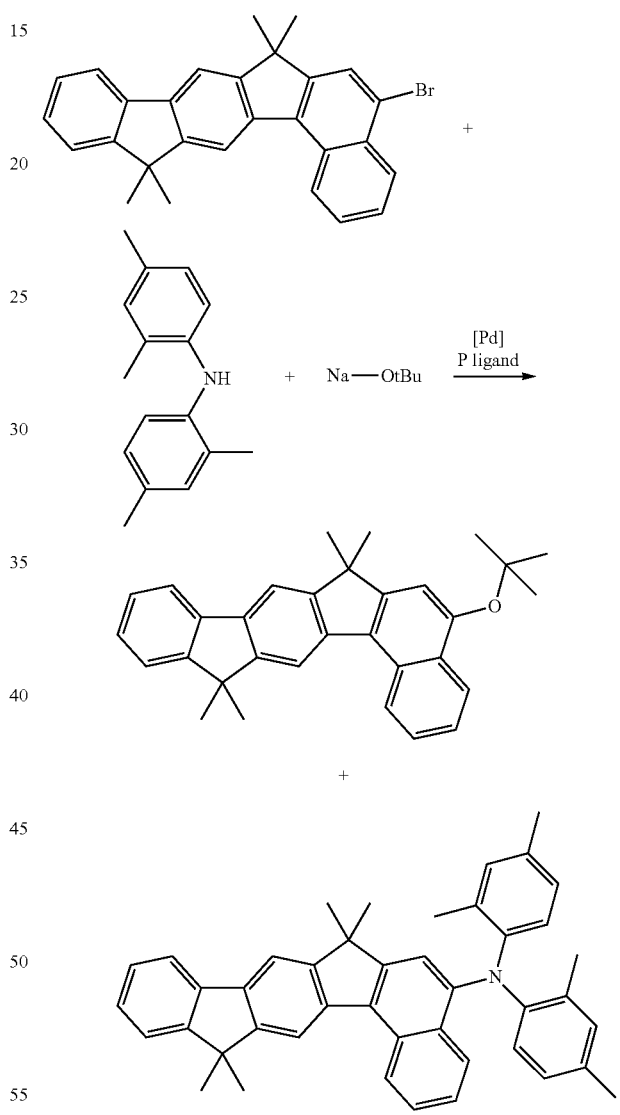

A mixture of sodium tert-butoxide (1.2 eq.), bis(2,4-dimethylphenyl)amine (1.25 eq), 1,2-benzo-3-bromo-6,6,12,12-tetramethyl-6,12-dihydroindeno-[1,2-b]fluorene (1 eq), Pd(OAc)$_2$ (0.02 eq) and 2-(dicyclohexylphosphino)-2',6'-dimethoxy)biphenyl (S-Phos, 0.04 eq) in toluene is heated under reflux for 2 h. After cooling to room temperature, water is added, the organic phase is separated off, dried using MgSO$_4$ and filtered through silica gel. The solvent is removed. The 1H-NMR spectrum of the residue shows product type A: by-product type NA=17:80.

Further examples with variation of ligand and starting-material type:

| Starting material type | Pd source | [P] ligand | Base | Ar | Yield [%] | Purity [%] |
|---|---|---|---|---|---|---|
| A | Pd(OAc)$_2$ | S-Phos | NaOtBu | 2,4-dimethylphenyl | Crude | 17 (A):80 (NA) |
| A | Pd(OAc)$_2$ | Ru-Phos | NaOtBu | 2,4-dimethylphenyl | Crude | 18 (A):79 (NA) |
| A | Pd(OAc)$_2$ | PPh$_3$ | NaOtBu | 2,4-dimethylphenyl | Crude | 15 (A):40 (NA) |
| A | Pd(OAc)$_2$ | PCltBu$_2$ | NaOtBu | 2,4-dimethylphenyl | 34 | 55 (A):18 (NA) |
| A | Pd(OAc)$_2$ | PtBu$_3$ | NaOtBu | 2,4-dimethylphenyl | 66 | 96.8 (A) |
| A | Pd(OAc)$_2$ | PtBu$_3$ | NaOtBu | 2,4-dimethylphenyl | 64 | 96.7 (A) |
| B | Pd(OAc)$_2$ | PtBu$_3$ | NaOtBu | 2,4-dimethylphenyl | 27 | 97.3 (B) |
| B | Pd(OAc)$_2$ | PtBu$_3$ | NaOtBu | 2,3-dimethylphenyl | 20 | 98.7 (B) |
| B | Pd(OAc)$_2$ | PCltBu$_2$ | NaOtBu | 2,3-dimethylphenyl | n. a. | 5 (B):90 (NB) |

Explanation of the Starting Material/Product Designations:

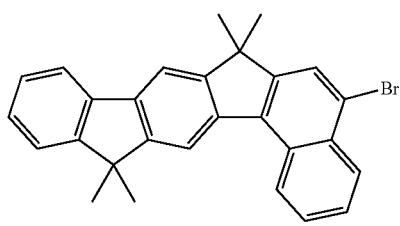

Starting material type A

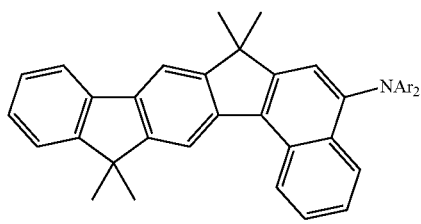

Product type A

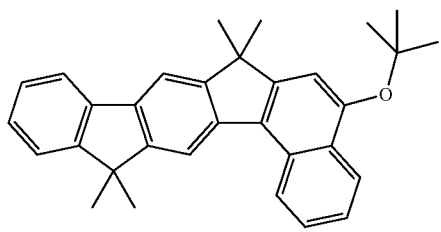

By-product type NA

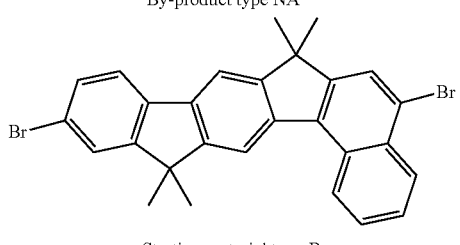

Starting material type B

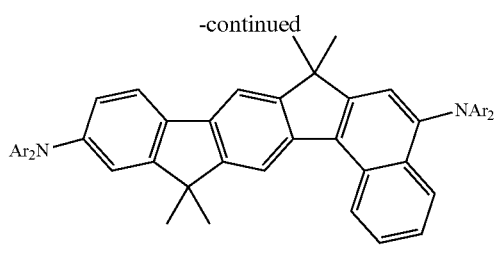

Product type B

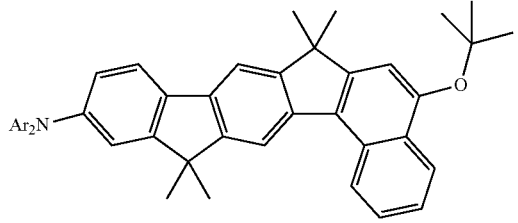

By-product type NB

C) Example According to the Invention

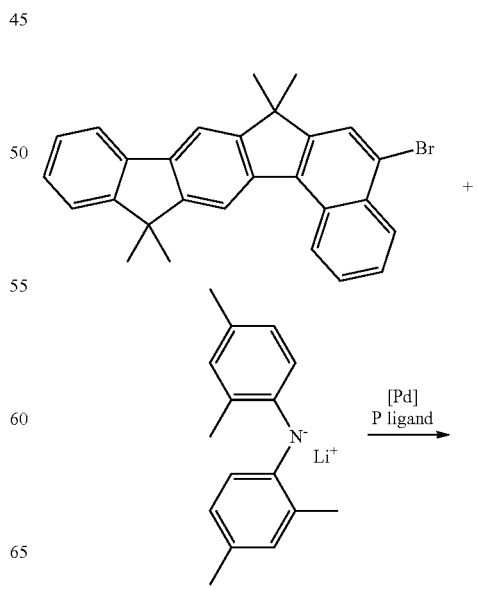

-continued

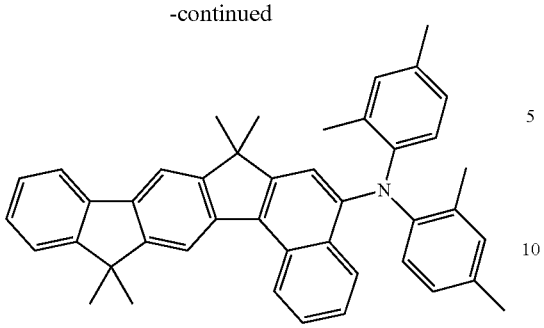

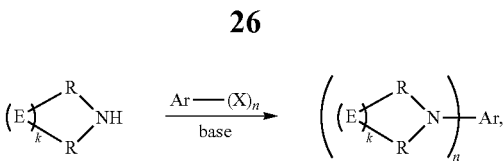

and the amino compound is of the formula

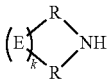

Hexyllithium (2.5 M in hexane, 1.2 eq.) is added dropwise to a solution of bis(2,4-dimethylphenyl)amine (1.25 eq), 1,2-benzo-3-bromo-6,6,12,12-tetramethyl-6,12-dihydroindeno[1,2-b]fluorene (1 eq), Pd(OAc)₂ (0.02 eq) and 2-(dicyclohexylphosphino)-2',6'-dimethoxy)biphenyl (S-Phos, 0.04 eq) in toluene, and the mixture is subsequently heated under reflux for 1 h. After cooling to room temperature, water is added, the organic phase is separated off, dried using MgSO₄ and filtered through silica gel. The solvent is removed, and the residue is washed with acetonitrile and isopropanol. Yield: 90%; purity; 99.2% (HPLC). The purity can be increased to 99.95% by Soxhlett extraction and sublimation.

Further Examples with Hexyllithium or LDA as Base:

| Starting material type | Pd source | [P] ligand | Base | Ar1 | Ar2 | Yield [%] | Purity [%] |
|---|---|---|---|---|---|---|---|
| A | Pd(OAc)₂ | S-Phos | Hex-Li | 2-methylphenyl | 2-methylphenyl | 93 | 99.3 |
| A | Pd(OAc)₂ | S-Phos | Hex-Li | 2,3-dimethylphenyl | 2,3-dimethylphenyl | 94 | 99.2 |
| A | Pd(OAc)₂ | S-Phos | Hex-Li | 2,4-dimethylphenyl | 2,4-dimethylphenyl | 90 | 99.2 |
| A | Pd(OAc)₂ | PPh₃ | Hex-Li | 2,4-dimethylphenyl | 2,4-dimethylphenyl | 79 | 98.5 |
| A | Pd(OAc)₂ | P(o-tol)₃ | Hex-Li | 2,4-dimethylphenyl | 2,4-dimethylphenyl | 88 | 98.0 |
| A | Pd(OAc)₂ | PCltBu₂ | Hex-Li | 2,4-dimethylphenyl | 2,4-dimethylphenyl | 90 | 99.0 |
| A | Pd(OAc)₂ | PtBu₃ | Hex-Li | 2,4-dimethylphenyl | 2,4-dimethylphenyl | 94 | 99.5 |
| A | Pd(OAc₃)₄ | — | Hex-Li | 2,4-dimethylphenyl | 2,4-dimethylphenyl | 81 | 98.8 |
| A | Pd(OAc)₂ | S-Phos | Hex-Li | 2,4-dimethylphenyl | 2,4,6-trimethylphenyl | 88 | 99.0 |
| A | Pd(OAc)₂ | S-Phos | LDA | 2-methylphenyl | 2-methylphenyl | 92 | 99.1 |
| A | Pd(OAc)₂ | S-Phos | LDA | 2,3-dimethylphenyl | 2,3-dimethylphenyl | 90 | 99.2 |
| A | Pd(OAc)₂ | S-Phos | LDA | 2,4-dimethylphenyl | 2,4-dimethylphenyl | 87 | 99.1 |
| B | Pd(OAc)₂ | S-Phos | Hex-Li | 2,3-dimethylphenyl | 2,3-dimethylphenyl | 92 | 98.5 |
| B | Pd(OAc)₂ | S-Phos | Hex-Li | 2,4-dimethylphenyl | 2,4-dimethylphenyl | 92 | 98.9 |

Explanation of the designations of the starting-material types: see above

D) $pK_a$ Values of the Bases Used ($K_3PO_4$, $K_2CO_3$ and $Cs_2CO_3$ are Very Weak Bases)

|  | $pK_a$ (DMSO) |
|---|---|
| NaOtBu (comparative example) | 29 |
| LDA (example according to the invention) | 44 |
| Hexyllithium (example according to the invention) | approx. 50 |

The invention claimed is:

1. A process for the preparation of a compound containing at least one arylamino group, the process comprising at least one palladium-catalysed coupling reaction between an amino compound, and an aryl compound, Ar—(X)$_n$, in the presence of a base having a $pK_a$ value based on dimethyl sulfoxide of at least 33, the process indicated by the following reaction scheme wherein:
Ar is an aromatic ring system having 10 to 30 aromatic ring atoms, optionally substituted by one or more radicals R¹, and includes a condensed aromatic ring system of at least two aromatic rings condensed with one another, where the one ring is condensed onto the other ring in an ortho-position to the bond to the amine nitrogen;
E is, identically or differently on each occurrence, selected from a single bond, C(R¹)₂, C=O, Si(R¹)₂, NR¹, O, and S;
R is, identically or differently on each occurrence, selected from H, a straight-chain alkyl group having 1 to 20 C atoms or a branched or cyclic alkyl group having 3 to 20 C atoms or an alkenyl or alkynyl group having 2 to 20 C atoms, optionally substituted by one or more radicals R¹ and where one or more CH₂ groups in the above-mentioned groups are optionally replaced by —R¹C=CR¹—, —C≡C—, Si(R¹)₂, C=O, C=S, C=NR¹, —C(=O)O—, —C(=O)NR¹—, NR¹, P(=O)(R¹), —O—, —S—, SO, or SO₂, and where one or more H atoms in the above-mentioned groups are optionally replaced by D, F, Cl, Br, I, CN or NO₂, or an aryl group having 5 to 60 aromatic ring atoms, optionally substituted by one or more radicals R¹,
where at least one R is an aryl group with a substituent R¹ in the ortho-position to the bond to the nitrogen atom, or at least one R is an aryl group with a condensed-on ring in the ortho-position to the bond to the nitrogen atom, and
where radicals R are optionally linked to one another to define a ring, and where not more than one group R on a nitrogen atom is equal to H;
R¹ is, identically or differently on each occurrence, selected from H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each optionally substituted by one or more radicals R² and where one or more CH₂ groups in the above-mentioned groups are optionally replaced by —R²C=CR²—, —C≡C—, Si(R²)₂, C=O, C=S, C=NR², —C(=O)O—, —C(=O)NR²—, NR², P(=O)(R²), —O—, —S—, SO, or SO₂, and where one or more H atoms in the above-mentioned groups are optionally replaced by D, F, Cl, Br, I, CN or NO₂, or an aromatic ring system having 5 to 30 aromatic ring atoms, which may in each case be substituted by one or more radicals R², or an aryloxy group having 5 to 30 aromatic ring atoms, optionally substituted by one or more radicals R², where two or more radicals R¹ are optionally linked to one another to define a ring;

R² is, identically or differently on each occurrence, H, D, F, or an aliphatic, aromatic, or heteroaromatic organic radical having 1 to 20 C atoms, wherein one or more H atoms are optionally replaced by D or F; two or more substituents R² are optionally linked to one another to define a ring;

X is, identically or differently on each occurrence, a leaving group;

k is, identically or differently on each occurrence, 0 or 1, wherein, if k=zero, the group E is not present; and n is a value of 1 to 10.

2. The process of claim 1, wherein the base has a pK_a value that is greater than the pK_a value of the amino compound by at least 6.

3. The process of claim 1, wherein the base has a pK_a value based on dimethyl sulfoxide of at least 34.

4. The process of claim 1, wherein the base has a pK_a value based on dimethyl sulfoxide of at least 36.

5. The process of claim 1, wherein the base is selected from amides with alkali-metal or alkaline-earth metal counterion and organometallic compounds containing a formally negatively charged carbon atom with alkali-metal or alkaline-earth metal counterion.

6. The process of claim 1, wherein the amino compound is a diarylamino compound.

7. The process of claim 1, wherein all groups R are not H.

8. The process of claim 1, wherein n is 1 or 2.

9. The process of claim 1, wherein the group Ar contains at least one radical R¹ in the ortho-position to the bond to the leaving group X which is other than H and D.

10. The process of claim 1, wherein the group Ar includes a condensed aryl group selected from naphthalene, anthracene, phenanthrene, pyrene, chrysene, perylene, fluoranthene, benzanthracene, benzophenanthrene, tetracene, pentacene, benzopyrene, acridine, or phenanthridine.

11. The process of claim 10, wherein the group Ar further includes an aromatic ring system selected from fluorene, spirobifluorene, cis- or trans-indenofluorene, cis- or trans-indolocarbazole, cis- or trans-indenocarbazole, cis- or trans-monobenzindenofluorene, and cis- or trans-dibenzindenofluorene.

12. The process of claim 1, wherein a crude product yield is of greater than 80% of the compound containing at least one arylamino group, and less than 20% of by-products selected from a defunctionalisation or coupling of the base.

13. A process for the preparation of a compound containing at least one arylamino group, the process comprising at least one palladium-catalysed coupling reaction between a diarylamino compound, and an aryl compound, Ar—(X)_n, in the presence of a base having a pK_a value of at least 36, based on dimethyl sulfoxide, and the pK_a value of the base is greater than the pK_a value of the amino compound by at least 6, the process indicated by the following reaction scheme

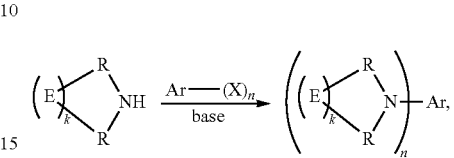

and the amino compound is of formula wherein:

Ar is an aromatic ring system having 10 to 30 aromatic ring atoms, optionally substituted by one or more radicals R¹, and includes a condensed aromatic ring system of at least two aromatic rings condensed with one another, where the one ring is condensed onto the other ring in an ortho-position to the bond to the amine nitrogen;

E is, identically or differently on each occurrence, selected from a single bond, C(R¹)₂, C=O, Si(R¹)₂, NR¹, O, and S;

R is, identically or differently on each occurrence, selected from H, a straight-chain alkyl group having 1 to 20 C atoms or a branched or cyclic alkyl group having 3 to 20 C atoms or an alkenyl or alkynyl group having 2 to 20 C atoms, optionally substituted by one or more radicals R¹ and where one or more CH₂ groups in the above-mentioned groups are optionally replaced by —R¹C=CR¹—, —C≡C—, Si(R¹)₂, C=O, C=S, C=NR¹, —C(=O)O—, —C(=O)NR¹—, NR¹, P(=O)(R¹), —O—, —S—, SO, or SO₂, and where one or more H atoms in the above-mentioned groups are optionally replaced by D, F, Cl, Br, I, CN or NO₂, or an aryl group having 5 to 60 aromatic ring atoms, optionally substituted by one or more radicals R¹, where at least one R is an aryl group with a substituent R¹ in the ortho-position to the bond to the nitrogen atom, or at least one R is an aryl group with a condensed-on ring in the ortho-position to the bond to the nitrogen atom, and where radicals R are optionally linked to one another to define a ring, and where not more than one group R on a nitrogen atom is equal to H;

R¹ is, identically or differently on each occurrence, selected from H, D, F, Cl, Br, I, B(OR²)₂, CHO, C(=O)R², CR²=C(R²)₂, CN, C(=O)OR², C(=O)N(R²)₂, Si(R²)₃, N(R²), NO₂, P(=O)(R²)₂, OSO₂R², OR², S(=O)R², S(=O)₂R², a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each optionally substituted by one or more radicals R² and where one or more CH₂ groups in the above-mentioned groups are optionally replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO, or $SO_2$, and where one or more H atoms in the above-mentioned groups are optionally replaced by D, F, Cl, Br, I, CN or $NO_2$, or an aromatic ring system having 5 to 30 aromatic ring atoms, which may in each case be substituted by one or more radicals $R^2$, or an aryloxy group having 5 to 30 aromatic ring atoms, optionally substituted by one or more radicals $R^2$, where two or more radicals $R^1$ are optionally linked to one another to define a ring;

$R^2$ is, identically or differently on each occurrence, H, D, F, or an aliphatic, aromatic, or heteroaromatic organic radical having 1 to 20 C atoms, wherein one or more H atoms are optionally replaced by D or F; two or more substituents $R^2$ are optionally linked to one another to define a ring;

X is, identically or differently on each occurrence, a leaving group;

k is, identically or differently on each occurrence, 0 or 1, wherein, if k=zero, the group E is not present; and n is 1 or 2.

14. The process of claim 13, wherein the group Ar includes a condensed aryl group selected from naphthalene, anthracene, phenanthrene, pyrene, chrysene, perylene, fluoranthene, benzanthracene, benzophenanthrene, tetracene, pentacene, benzopyrene, acridine, or phenanthridine.

15. The process of claim 14, wherein a crude product yield is of greater than 90% of the compound containing at least one arylamino group, and less than 10% of by-products selected from a defunctionalisation or coupling of the base.

16. The process of claim 13, wherein one or both aryl groups of the diarylamino compound includes a substituent in the ortho position to the amine nitrogen selected from an alkyl group having 1 to 10 C atoms, which may be substituted by one or more radicals $R^2$, or an aryl groups having 5 to 18 aromatic ring atoms, which may be substituted by one or more radicals $R^2$, or the diarylamino group an aryl group includes a condensed-on ring in the ortho-position to the bond to the amine nitrogen.

* * * * *